(12) United States Patent
Turnbaugh, Jr. et al.

(10) Patent No.: US 7,183,114 B2
(45) Date of Patent: Feb. 27, 2007

(54) METHOD FOR THE ANALYSIS OF GAS PRODUCED BY A TITANIUM TETRACHLORIDE FLUIDIZED BED REACTOR

(75) Inventors: Donald Theodore Turnbaugh, Jr., Oklahoma City, OK (US); Alan J. Morris, Oklahoma City, OK (US); Johnny Balcom Perkins, Hamilton, MS (US)

(73) Assignee: Tronox LLC, Oklahoma City, OK (US)

( * ) Notice: Subject to any disclaimer, the term of this patent is extended or adjusted under 35 U.S.C. 154(b) by 709 days.

(21) Appl. No.: 10/440,702

(22) Filed: May 19, 2003

(65) Prior Publication Data

US 2004/0235179 A1    Nov. 25, 2004

(51) Int. Cl.
G01N 33/00 (2006.01)
G01N 35/08 (2006.01)
H05F 3/00 (2006.01)
C02F 1/72 (2006.01)

(52) U.S. Cl. .................... 436/34; 436/55; 204/164; 210/758

(58) Field of Classification Search ............. 436/34, 436/55; 204/164
See application file for complete search history.

(56) References Cited

U.S. PATENT DOCUMENTS 2,701,179 A   2/1955   McKinney
2,790,703 A   4/1957   Frey (Continued)

OTHER PUBLICATIONS van Woerkom et al., Infrared emission spectra from a heterogenous catalyst system in reaction conditions. 1: Description of the microreactor assembly, Aug. 1, 1980, Applied Optics, v. 19, No. 15, pp. 2546-2550.*

(Continued)

*Primary Examiner*—Jill Warden
*Assistant Examiner*—Lore Ramillano
(74) *Attorney, Agent, or Firm*—Timothy S. Stevens

(57) ABSTRACT

A method to determine the concentration ratio of carbon monoxide to carbon dioxide in the gaseous product of a fluidized bed reactor for producing titanium tetrachloride. The hot fluidized bed of the reactor is used as the source of infrared radiation which radiation is directed through the gaseous products in upper portion of the reactor through a window in the reactor to an infrared spectrometer. The concentration ratio can be used to control the temperature of the fluidized bed reactor by controlling the amount of cool titanium tetrachloride that is introduced into the reactor.

4 Claims, 4 Drawing Sheets

U.S. PATENT DOCUMENTS

| | | | |
|---|---|---|---|
| 3,526,477 | A | 9/1970 | Wan |
| 3,591,333 | A | 7/1971 | Carson et al. |
| 3,883,636 | A | 5/1975 | Cole et al. |
| 4,046,854 | A | 9/1977 | Dunderdale |
| 4,619,815 | A | 10/1986 | Robinson |
| 4,854,972 | A | 8/1989 | Garrido et al. |
| 4,961,911 | A | 10/1990 | Reis et al. |
| 5,389,353 | A | 2/1995 | Glaeser et al. |
| 5,585,078 | A | 12/1996 | Reis et al. |
| 5,670,121 | A | 9/1997 | Elkins |
| 5,984,998 | A * | 11/1999 | Ottesen et al. ............... 75/375 |
| 6,284,196 | B1 * | 9/2001 | Casal et al. ................. 422/62 |

OTHER PUBLICATIONS

Clausen et al., Infrared low resolution emission spectroscopy of hot gases, Apr. 1998, SPIE, v. 3383, pp. 133-139.*

Soufiani et al., Sensitivity of temperature and concentration measurements in hot gases from FTIR emission spectroscopy, 2002, Journal of Quantitatives Spectroscopy & Radiative Transfer, v. 73, No. 2-5, pp. 317-327.*

Hilton et al.; Gas turbine exhaust emissions monitoring using noninstrusive infrared spectroscopy, 1998, Journal of Engineering for Gas Turbines and Power, v. 120, No. 3, pp. 514-518.*

Arunan et al., Vibrational-relaxation rate constants for hydrogen fluoride (v=1-4) by carbon monoxide, carbon dioxide, and hydrogen cyanide with product identification by infrared emission, 1992, Journal of Chemical Physics, v. 97, No. 9, pp. 6348-6362.*

1997 Kirk-Othmer Encyclopedia of Chem Tech. 4th Ed vol. 24 1988 Pigment Handbook, Lewis 2nd Ed.

* cited by examiner

METHOD FOR THE ANALYSIS OF GAS PRODUCED BY A TITANIUM TETRACHLORIDE FLUIDIZED BED REACTOR

BACKGROUND

The chloride process for producing titanium dioxide is well known, see Volume 24 of the Kirk-Othmer Encyclopedia of Chemical Technology (4$^{th}$ Ed., 1997) and in Volume I of the Pigment Handbook, Edited by Lewis (2$^{nd}$ Ed., 1988). The first step of the chloride process for producing titanium dioxide is the chlorination of a titanium bearing material (for example, rutile ore) in a fluidized bed reactor, see U.S. Pat. Nos. 2,701,179; 2,790,703; 3,526,477; 3,883,636; 3,591,333; 4,046,854; 4,619,815; 4,854,972; 4,961,911; 5,389,353; 5,670,121; and 5,585,078 (all of which are fully incorporated herein by reference). In summary, the titanium bearing material, a source of carbon (usually coke) and chlorine are reacted (for example at 900–1300 degrees Celsius) in a fluidized bed at the lower portion of the reactor to produce a gaseous stream comprising titanium tetrachloride, carbon monoxide; carbon dioxide and carbonyl sulfide, which gaseous stream moves to the upper portion of the reactor and then is exhausted from the reactor for further processing.

According to the teachings of the above-referenced '121 patent: (a) it is desirable in such a reactor to minimize the formation of carbon monoxide to decrease the amount of carbon required per unit of titanium tetrachloride produced; and (b) it is desirable to decrease the formation of carbonyl sulfide because carbonyl sulfide is an undesired byproduct. According to the teachings of the '121 patent, the formation of carbon monoxide and carbonyl sulfide can be reduced by cooling the fluidized bed, such as by introducing a suitable cooling material (such as titanium tetrachloride at 100 degrees Celsius) into the reactor above the fluidized bed. However, according to the teachings of the '121 patent, if the fluidized bed is overcooled, then the concentration of unreacted chlorine tends to increase to undesirable levels in the gaseous stream from the reactor. Thus, there appears to be an optimum temperature of the fluidized bed in the reactor which temperature can be controlled by, for example, controlling the amount of cooling material introduced into the reactor above the fluidized bed. According to the teachings of the above-referenced '911 patent, chlorine can be added just above the surface of the fluidized bed to convert carbon monoxide to carbon dioxide. According to the teachings of the above-referenced '078 patent, oxygen can be added to the reactor to convert carbon monoxide to carbon dioxide and to convert carbonyl sulfide to sulfur dioxide.

With the above in view, it is apparent that a number of different improvements have been made to the fluidized bed process for converting titanium dioxide to titanium tetrachloride so that the concentration of undesirable byproducts of the process can be reduced. For example, formation of undesirable carbon monoxide can be reduced and/or carbon monoxide can be converted to carbon dioxide. And, the formation of undesirable carbonyl sulfide can similarly be reduced and/or the carbonyl sulfide can be converted to sulfur dioxide. Whatever improved process is used to reduce the concentration of undesirable components (such as carbon monoxide and/or carbonyl sulfide) the gaseous exhaust stream from the reactor can be analyzed to control the improved process. For example, the '121 patent disclosed the use of a Fourier transform infrared analyzer to analyze the exhaust gas stream from the reactor (after the titanium tetrachloride was condensed therefrom) for carbonyl sulfide.

Analysis of the exhaust gas stream from the reactor is difficult because the stream is hot, corrosive and contains particulates. Analysis of the exhaust gas stream after the titanium tetrachloride has been condensed therefrom is more favorable but still problematic because, for example, the required sampling systems tend to corrode and plug. It would be an advance in the art of chemical analysis of the gasses from a fluidized bed reactor for making titanium tetrachloride if components therein (such as carbon monoxide, carbon dioxide, carbonyl sulfide and sulfur dioxide) could be determined without the need to extract a sample thereof and especially if the determination were related to a concentration ratio of one undesired component to another related more desirable component (such as the concentration ratio of carbon monoxide to carbon dioxide or the concentration ratio of carbonyl sulfide to sulfur dioxide).

SUMMARY OF THE INVENTION

The instant invention in one aspect provides a chemical analysis method for the analysis of components in gases produced by a fluidized bed reactor for making titanium tetrachloride, which method does not require a sampling system. The instant invention uses a totally different approach. The instant invention provides a method to determine the ratio of infrared absorption intensity of a first component (such as carbon monoxide or carbonyl sulfide) to a second component (such as carbon dioxide or sulfur dioxide) in the gaseous product of a fluidized bed reactor for producing titanium tetrachloride. The instant invention uses the hot fluidized bed of the reactor as the source of infrared radiation and directs this radiation through the gaseous products in an upper portion of the reactor through a window in the reactor to an infrared spectrometer to determine the intensity of infrared radiation of at least a first wavenumber, a second wavenumber, and a third wavenumber, the first wavenumber being a wavenumber where the first component has a higher absorbance per volume percent than the second component, the second wavenumber being a wavenumber where the second component has a higher absorbance per volume percent than the first component, and the third wavenumber being a wavenumber where both the first component and the second component have a relatively low absorbance per volume percent. Then, the absorption intensity of the first component is determined by comparing the intensity of the infrared radiation at the first and third wavenumbers, and the absorption intensity of the second component is determined by comparing the intensity of the infrared radiation at the second and third wavenumbers. Finally, the ratio of infrared absorption intensity of the first component to the second component in the gaseous product at the upper portion of the reactor is determined by dividing the absorption intensity of the first component by the absorption intensity of the second component. The concentration ratio of the first component to the second component can be determined, for example, if the log of the absorption intensity of the first component is divided by the log of the absorption intensity of the second component and the product is multiplied by a calibration factor.

In another aspect, the instant invention provides an improved process for controlling the temperature of a fluidized bed reactor in the manufacture of titanium tetrachloride, wherein the manufacture of titanium tetrachloride comprises the steps of feeding carbonaceous material, titanium bearing material, and chlorine to a fluidized bed reactor to react in a fluidized bed to form titanium tetrachloride and an exhaust gas stream comprising carbon monoxide and carbon dioxide, the exhaust gas stream being directed to a condenser. The improvement comprises seven steps. The first step is to direct infrared radiation from the fluidized bed through the upper portion of the reactor to an infrared spectrometer to determine the intensity of infrared radiation of at least a first wavenumber, a second wavenumber and a third wavenumber, the first wavenumber being a wavenumber where carbon monoxide has a higher absorbance per volume percent than carbon dioxide, the second wavenumber being a wavenumber where carbon dioxide has a higher absorbance per volume percent than carbon monoxide, and the third wavenumber being a wavenumber where carbon monoxide and carbon dioxide have a relatively low absorbance per volume percent. The second step is to determine the absorption intensity of carbon monoxide by comparing the intensity of the infrared radiation at the first and third wavenumbers. The third step is to determine the absorption intensity of carbon dioxide by comparing the intensity of the infrared radiation at the second and third wavenumbers. The fourth step is to determine the infrared absorption intensity ratio of carbon monoxide to carbon dioxide in the gaseous product at the upper portion of the reactor by dividing the absorption intensity of the second step by the absorption intensity of the third step. The fifth step is to determine the desired infrared absorption intensity ratio of carbon monoxide to carbon dioxide in the gaseous product at the upper portion of the reactor. The sixth step is to calculate the difference between the infrared absorption intensity ratio of carbon monoxide to carbon dioxide in the gaseous product at the upper portion of the reactor and the desired infrared absorption intensity ratio of carbon monoxide to carbon dioxide in the gaseous product at the upper portion of the reactor. The seventh step is generate a signal which corresponds to the difference calculated in the sixth step and provide a feedback response to the fluidized bed reactor to control the temperature of the fluidized bed reactor.

DETAILED DESCRIPTION OF PREFERRED EMBODIMENTS OF THE INVENTION

Figure 1:
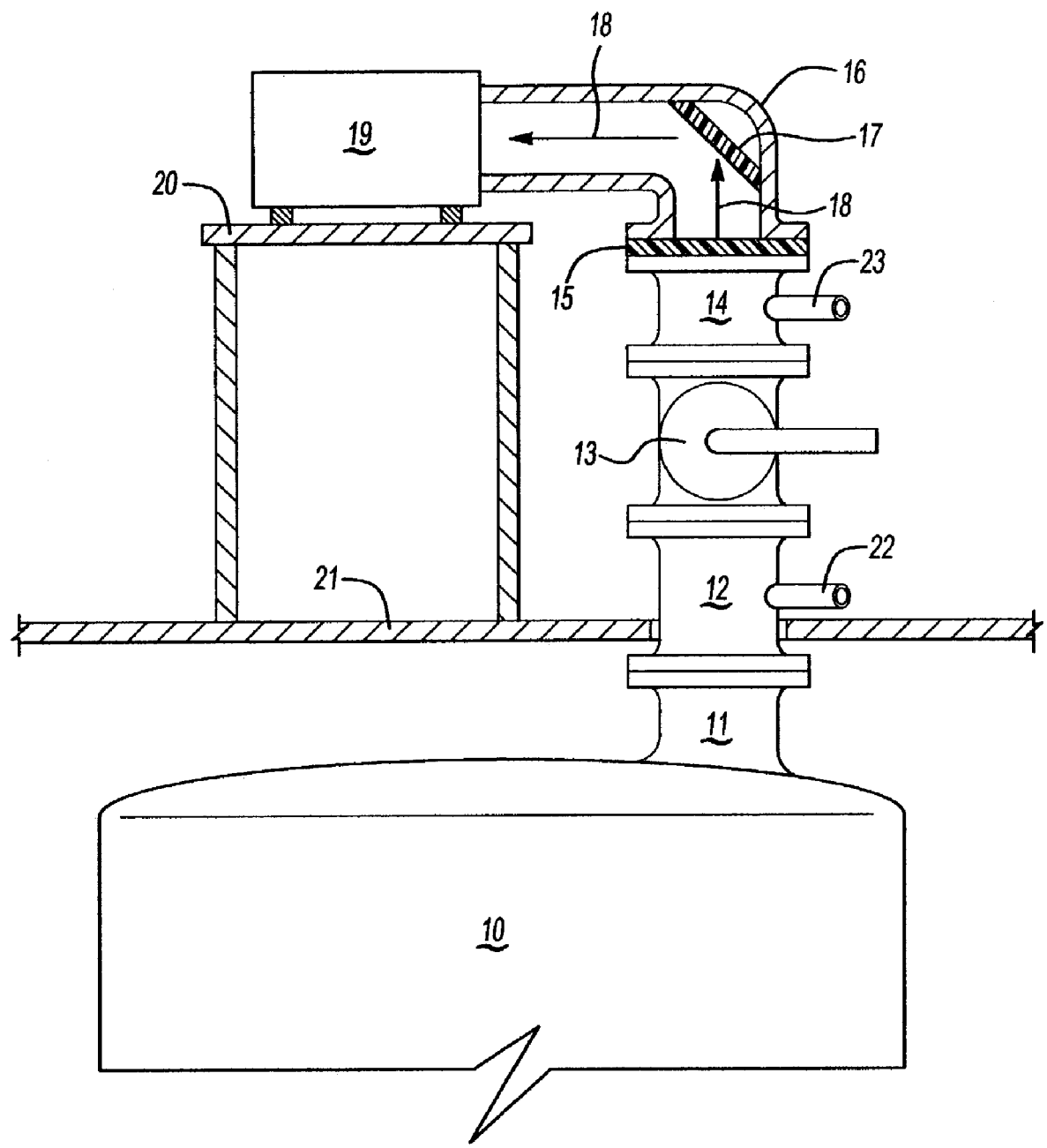
FIG. 1 is a side view, of the upper portion of a fluidized bed reactor for the production of titanium tetrachloride, the reactor having a flanged nozzle on the top of the reactor in communication with a sapphire window mounted in piping components connected to the nozzle so that infrared light from the reactor can be directed through the window to a Fourier transform infrared spectrometer by way of a mirror mounted in a piping elbow.

Referring now to FIG. 1, therein is shown a side view, of the upper portion of a fluidized bed reactor 10 for the production of titanium tetrachloride, the reactor 10 having a three inch diameter flanged nozzle 11 on the top of the reactor. A first three inch diameter flanged spool 12 is attached to the flanged nozzle 11. A three inch diameter flanged ball valve 13 is attached to the first spool 12. A second three inch diameter flanged spool 14 is attached to the valve 13. A sapphire window 15 (shown in cross section) is sandwiched between the spool 14 and a three inch diameter flanged elbow 16 (shown in cross section). An infrared mirror 17 (shown in cross section) reflects infrared light 18 from the reactor 10 (assuming the ball valve 13 is open) to a Fourier transform infrared spectrometer 19. The spectrometer 19 is positioned on an instrument table 20 (shown in cross section) that rests on deck 21 (also shown in cross section). First spool 12 is fitted with a line 22 so that nitrogen can be flowed into the first spool 12 to help prevent contamination of the window 15 by gas generated in the reactor 10. Second spool 14 is similarly fitted with a line 23 so that nitrogen can be flowed into the second spool 14 to help prevent contamination of the window 15 by gas generated in the reactor 10. The valve 13 can be closed for installation or maintenance purposes even if the reactor 10 is in operation.

Referring still to FIG. 1, the reactor 10 is fed with carbonaceous material, titanium bearing material, and chlorine to react in a fluidized bed near the bottom portion of the reactor 10 to produce a gaseous product that moves to the upper portion of the reactor 10, the gaseous product comprising titanium tetrachloride, carbon monoxide and carbon dioxide that is exhausted from the reactor 10 and directed to a condenser. The infrared radiation 18 from the fluidized bed in the reactor 10 is directed through the upper portion of the reactor 10 to the infrared spectrometer 19 to determine the intensity of infrared radiation of at least a first wavenumber, a second wavenumber and a third wavenumber, the first wavenumber being a wavenumber where carbon monoxide has a higher absorbance per volume percent than carbon dioxide, the second wavenumber being a wavenumber where carbon dioxide has a higher absorbance per volume percent than carbon monoxide, and the third wavenumber being a wavenumber where carbon monoxide and carbon dioxide have a relatively low absorbance per volume percent.

Figure 2:
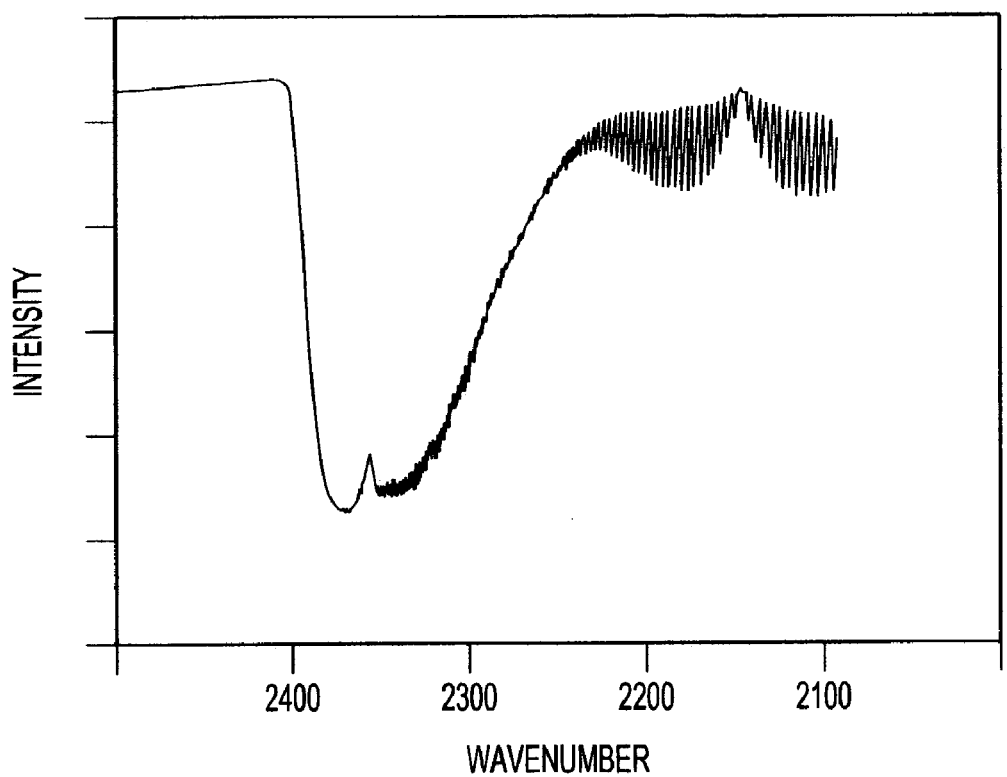
FIG. 2 is a plot of infrared radiation intensity on the vertical axis of the plot versus wavenumber on the horizontal axis of the plot as determined using the Fourier transform infrared spectrometer of FIG. 1.

Referring now to FIG. 2, therein is shown a scan of infrared radiation intensity from about 2450 wavenumbers to about 2100 wavenumbers obtained during operation of the reactor 10 of FIG. 1. The decrease in the intensity of infrared radiation in the range of from about 2240 to about 2400 wavenumbers is due to carbon dioxide. The decrease in the intensity of infrared radiation in the range of from about 2100 to about 2220 wavenumbers is due to carbon monoxide. Therefore, the first wavenumber associated with carbon monoxide can be selected from a wavenumber in the range of 2100 to 2220. If an essentially single wavenumber is selected, then it is preferable that it be the wavenumber where carbon monoxide has its maximum decrease in intensity (near 2120 wavenumbers or near 2180 wavenumbers). However, most preferably, the infrared intensity between 2096 and 2137 wavenumbers is integrated. Similarly, the second wavenumber associated with carbon dioxide can be selected from a wavenumber in the range of 2240 to 2400. If an essentially single wavenumber is selected, then it is preferable that it be the wavenumber where carbon dioxide has its maximum decrease in intensity (near 2370 wavenumbers or near 2330 wavenumbers). However, most preferably, the infrared intensity between 2243 and 2410 wavenumbers is integrated. The third wavenumber is most preferably 2400 wavenumbers. It should be understood that although it is preferable to use a Fourier transform infrared spectrometer system in the instant invention, other infrared spectrometers can be used such as a nondispersive infrared spectrometer, for example, a three filter nondispersive infrared spectrometer.

The absorption intensity of carbon monoxide is determined by comparing the intensity of the infrared radiation at the first and third wavenumbers. The absorption intensity of carbon dioxide is determined by comparing the intensity of the infrared radiation at the second and third wavenumbers. The infrared absorption intensity ratio of carbon monoxide to carbon dioxide is determined by dividing the absorption intensity for carbon monoxide by the absorption intensity for carbon dioxide. If the log of the absorption intensity of carbon monoxide is divided by the log of the absorption intensity of carbon dioxide, then the result is proportional to the concentration ratio of carbon monoxide to carbon dioxide (for example in terms of volume percent) and can be calculated by multiplying the result by a calibration factor.

Figure 3:
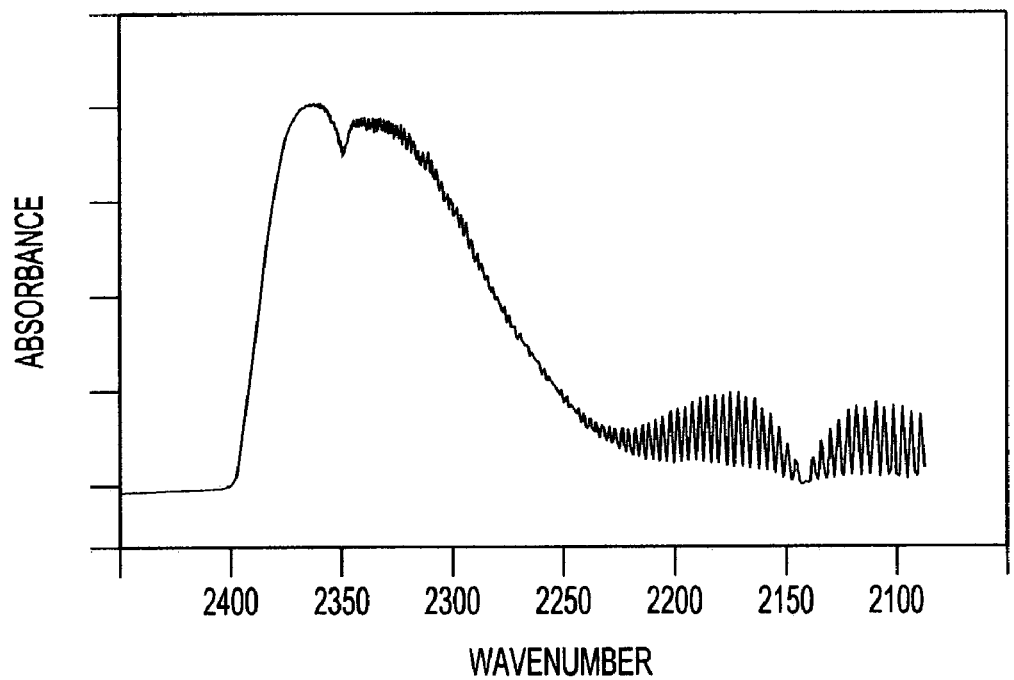
FIG. 3 is a plot of infrared absorbance on the vertical axis of the plot versus wavenumber on the horizontal axis of the plot as determined using the Fourier transform infrared spectrometer of FIG. 1.

It should be understood that the instant invention can be used to determine the ratio of infrared absorption intensity of components other than carbon monoxide and carbon dioxide, such as, for example, carbonyl sulfide and sulfur dioxide. Referring now to FIG. 3, therein is shown the data of FIG. 2 but wherein the vertical axis is presented in terms of absorbance rather than intensity using 2400 wavenumbers as the reference wavenumber.

Figure 4:
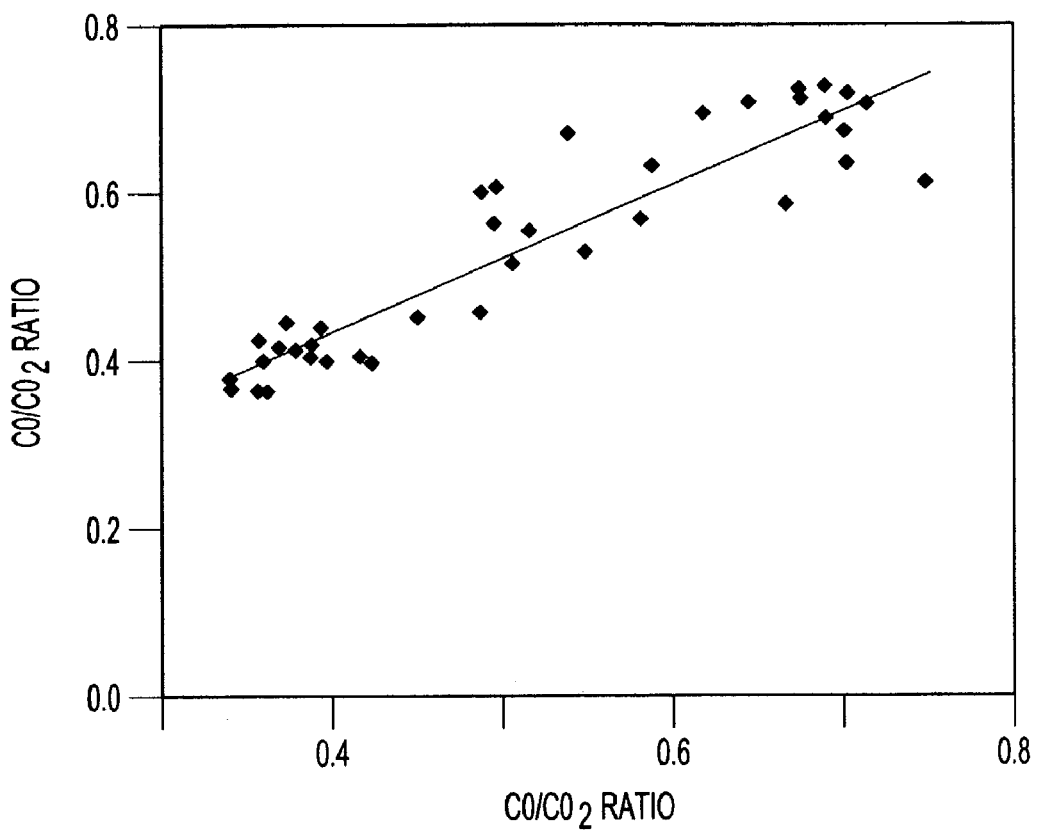
FIG. 4 is a plot of the infrared absorbance ratio of carbon monoxide to carbon dioxide as determined using the method of the instant invention on the vertical axis of the plot versus the volume percent ratio of carbon monoxide to carbon dioxide as determined using a prior art reference method on the horizontal axis of the plot.

Referring now to FIG. 4, therein is shown a plot of the infrared absorbance ratio of carbon monoxide to carbon dioxide as determined using the method of the instant invention on the vertical axis of the plot (using the system shown in FIG. 1 wherein the fluidized bed of the reactor is controlled at different temperatures thereby causing the volume percent ratio of carbon monoxide to carbon dioxide to vary in the range of from about 0.3 to about 0.8) versus the volume percent ratio of carbon monoxide to carbon dioxide as determined using a prior art reference method on the horizontal axis of the plot. The prior art reference method used a nondispersive infrared analyzer installed after the condenser to determine the carbon monoxide and carbon dioxide concentrations in the gas stream. During the collection of the data shown in FIG. 4, only a single fluidized bed reactor was operated so that a gas sample representative of the reactor was analyzed by the nondispersive infrared analyzer. The data in FIG. 4 shows the excellent correlation between the infrared absorbance ratio of carbon monoxide to carbon dioxide as determined using the method of the instant invention and the prior art reference method, despite the varying temperature conditions in the reactor.

Figure 5:
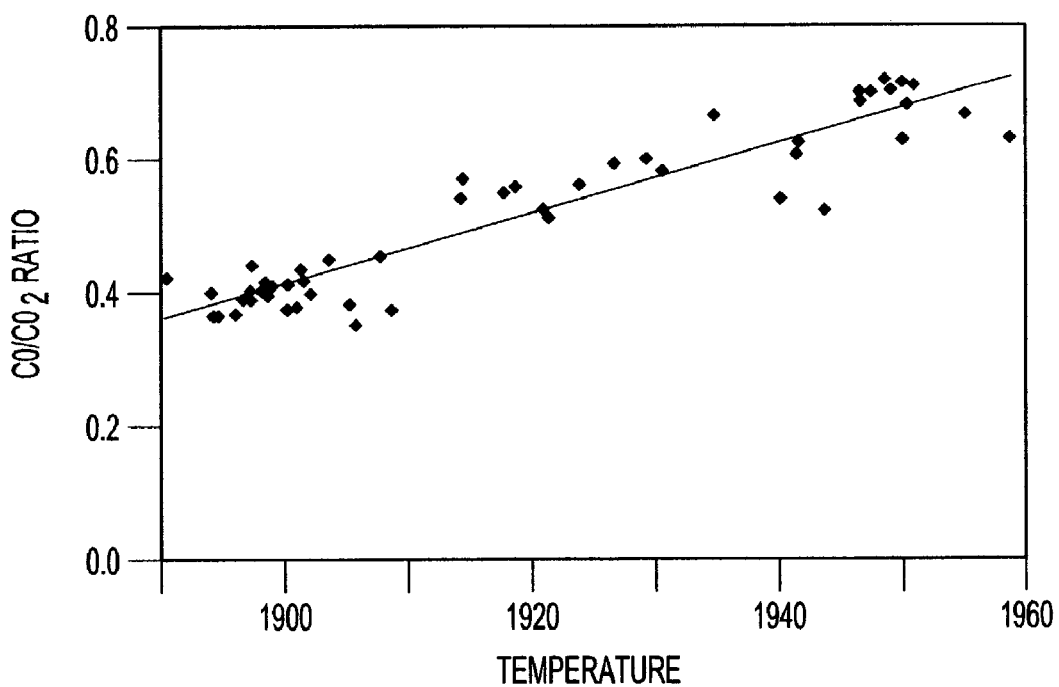
FIG. 5 is a plot of the infrared absorbance ratio of carbon monoxide to carbon dioxide as determined using the method of the instant invention on the vertical axis of the plot versus the temperature of the fluidized bed of FIG. 1 on the horizontal axis of the plot.

Referring now to FIG. 5, therein is shown a plot of the infrared absorbance ratio of carbon monoxide to carbon dioxide as determined using the method of the instant invention on the vertical axis of the plot versus the temperature (in degrees Farenheit) of the fluidized bed of FIG. 1 on the horizontal axis of the plot. The data in FIG. 5 shows the excellent correlation between the infrared absorbance ratio of carbon monoxide to carbon dioxide as determined using the method of the instant invention and the temperature of the fluidized bed in the reactor. Such a correlation can be used in a system to control the temperature of the fluidized bed in the reactor according to another aspect of the instant invention.

Figure 6:
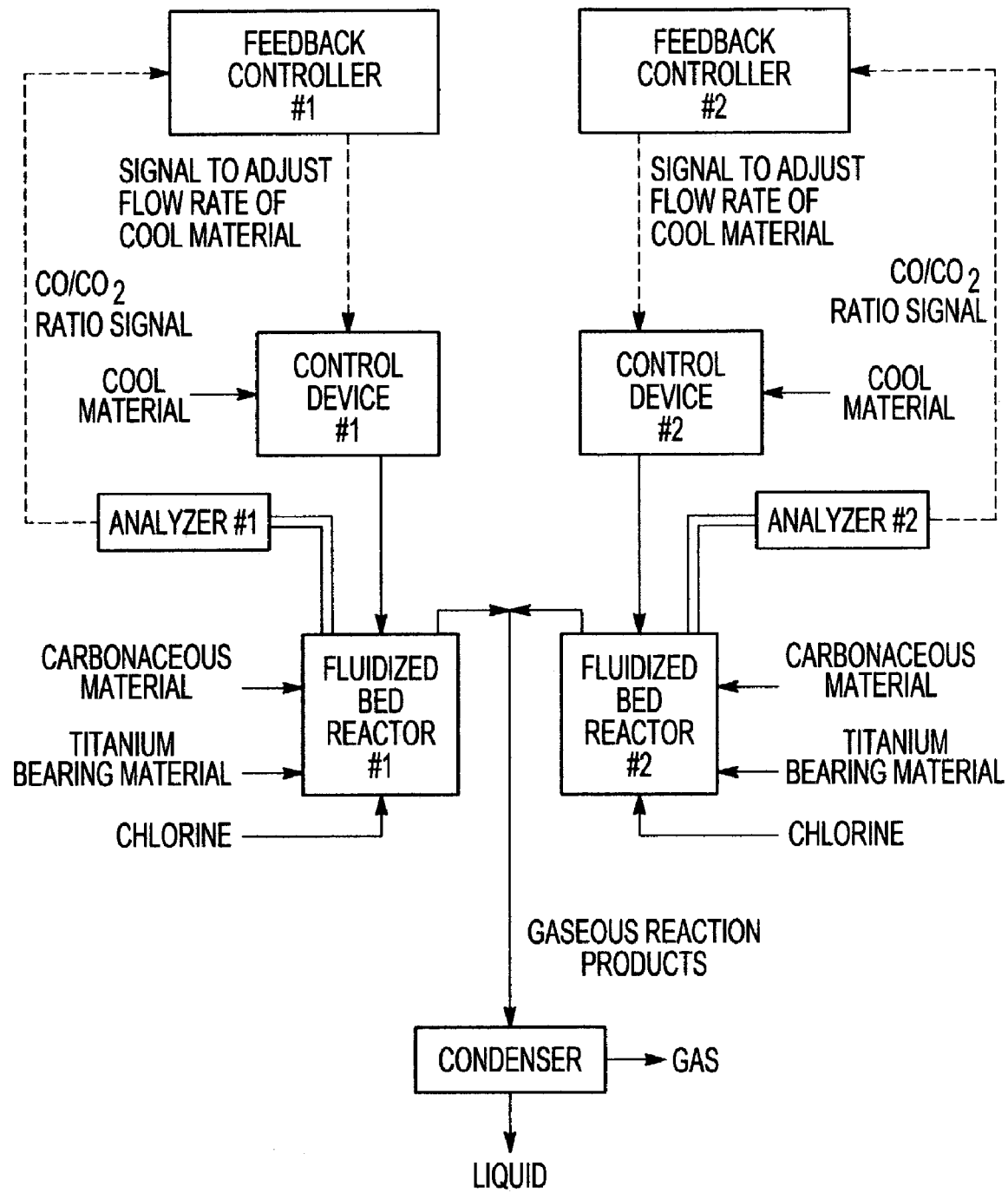
FIG. 6 is schematic diagram showing two fluidized bed reactors connected to one condenser and illustrating an improved process for controlling the temperature of each reactor according to an embodiment of the instant invention.

Referring now to FIG. 6, therein is shown a schematic diagram depicting two fluidized bed reactors connected to one condenser and illustrating an improved process for controlling the temperature of each reactor according to a preferred embodiment of the instant invention. Carbonaceous material (such as coke), titanium bearing material (such as rutile ore) and chlorine are fed into each reactor. Gaseous reaction products from each reactor are fed to a condenser system to recover titanium tetrachloride in the liquid stream from the condenser and a gas stream comprising carbon monoxide, carbon dioxide and any unreacted chlorine. Analyzer #1 and Analyzer #2 send a $CO/CO_2$ ratio signal (electrical, pneumatic, digital etc.), related to the infrared absorption intensity ratio of carbon monoxide to carbon dioxide in the gaseous product at the upper portion of the reactors to a pair of control systems (such as a distributed control system or other feedback control system) where its value is compared to a set point or determined as either within or without a set range.

If the infrared absorbtion intensity ratio of carbon monoxide to. carbon dioxide (the "controlled variable") of either reactor does not equal the set point or is outside of the set range, then the difference between the measured controlled variable and the set point is determined and a second signal (electrical, pneumatic, digital , etc.) corresponding to this difference is generated manually or preferably by a suitable feedback controller such as, for example, a proportional integral or a proportional integral derivative action controller or other suitable computer software or algorithm that provides a feedback response. Such feedback response causes a change in the amount of cool material being added to each reactor by making a proportional change in the flow rate of the cool material to each reactor by way of a pair of control devices. Preferably the control devices are automatic flow control valves.

The cool material added to control the temperature of each reactor can be any cool material that does not substantially adversely impact the production of titanium tetrachloride or interfere with the analysis of the instant invention. Most preferably, the cool material is titanium tetrachloride at, for example, about one hundred degrees Celsius.

It will be appreciated that when a plurality of fluidized bed reactors are connected to a single condenser (as shown in FIG. 6), then the temperature control process taught in U.S. Pat. No. 5,670,121 (wherein the gas from the condenser is analyzed) will not be effective because the exhaust gas streams from each reactor are mixed in the condenser. In the instant invention each such reactor has its own analyzer thereby providing an analysis of the gas produced in each reactor before any mixing thereof in the condenser and thereby allowing a system for the effective control of the temperature of each reactor.

What is claimed is:

1. A chemical analysis method for determining the ratio of infrared absorption intensity of a first component to a second component in a gaseous product of a fluidized bed reactor for producing titanium tetrachloride by reacting materials comprising titanium dioxide, carbon and chlorine in a fluidized bed at the lower portion of the reactor to produce a gaseous product that moves to the upper portion of the reactor, the gaseous product comprising titanium tetrachloride, the first component and the second component, the method comprising the steps of: (a) directing infrared radiation from the fluidized bed through the upper portion of the reactor to an infrared spectrometer to determine the intensity of infrared radiation of at least a first wavenumber, a second wavenumber and a third wavenumber, the first wavenumber being a wavenumber where the first component has a higher absorbance per volume percent than the second component, the second wavenumber being a wavenumber where the second component has a higher absorbance per volume percent than the first component, and the third wavenumber being a wavenumber where the first component and the second component have a relatively low absorbance per volume percent; (b) determining the absorption intensity of the first component by comparing the intensity of the infrared radiation at the first and third wavenumbers; (c) determining the absorption intensity of the second component by comparing the intensity of the infrared radiation at the second and third wavenumbers; and (d) determining the infrared absorption intensity ratio of the first component to the second component in the gaseous product at the upper portion of the reactor by dividing the absorption intensity of step (b) by the absorption intensity of step (c).

2. The method of claim 1, wherein in step (d) the log of the absorption intensity of step (b) is divided by the log of the absorption intensity of step (c) and the product is multiplied by a calibration factor to determine the concentration ratio of the first component to the second component.

3. The method of claim 2, wherein the first component is carbon monoxide and the second component is carbon dioxide.

4. The method of claim 1, wherein the first component is carbon monoxide and the second component is carbon dioxide.

* * * * *